United States Patent [19]

Cole

[11] Patent Number: Plant 7,690

[45] Date of Patent: Oct. 29, 1991

[54] IMPATIENS PLANT NAMED PEACH ICE

[76] Inventor: Douglas S. Cole, R.F.D. 13, Box 240, Concord, N.H. 03301

[21] Appl. No.: 514,206

[22] Filed: Apr. 25, 1990

[51] Int. Cl.[5] ..... A01H 5/00

[52] U.S. Cl. ..... Plt./68

[58] Field of Search ..... Plt./68, 87.6

[56] References Cited

U.S. PATENT DOCUMENTS

P.P. 7,130 1/1990 Simchock ..... Plt. 68

*Primary Examiner*—Howard J. Locker

*Attorney, Agent, or Firm*—Foley & Lardner

[57] ABSTRACT

A new cultivar of *Impatiens sultanii* plant named Peach Ice, characterized by its pinkish peach flower color, its fully double consistent flowers, and its variegated foliage with the light yellow variegation variably extending from the edge toward the leaf midrib.

1 Drawing Sheet

The present invention comprises a new and distinctive cultivar of Impatiens plant, botanically known as *Impatiens sultanii,* and known by the cultivar name Peach Ice. The species name appears to be synonymous with the species designation *Impatiens wallerana,* also referred to in botanical literature.

The new cultivar is a sport or mutation of the cultivar Rosebud Salmon, and was discovered by me in approximately December 1988 in greenhouses in Loudon, N.H. The mutation was discovered while taking cuttings of the parent cultivar, when one branch of one plant displayed variegated foliage, as opposed to the solid green foliage of the parent cultivar Rosebud Salmon. The branch cutting was removed, planted, and grown out, with the variegation and foliage being commonly displayed throughout the plant. Subsequent asexual reproduction by terminal or stem cuttings taken by the inventor in London, N.H. has shown that the unique features of this new cultivar are stabilized and are reproduced true to type in successive propagations.

The following characteristics taken in combination distinguish the new cultivar Peach Ice from both its parent and other cultivated *Impatiens sultanii* of this type known and used in the floriculture industry:

1. Fully double, consistent blooms.
2. Even growing, well shaped, mounded plant habit. Reasonably self-branching if propagated from a vegetative cutting.
3. Rooting time is approximately seven days to initiate roots at 70° F.; saleable cuttings are available in 21 days at 70° F.
4. The highest quality cuttings are produced by removing from approximately 3" stem and leaf cuttings a ¼"–½" tip and discarding it. The remaining cutting then branches much better.
5. The foliage is normally green in the center surrounded by distinct white edges. At times when it is newly potted and growing extremely rapidly the white margin will become thinner and the green center will have a silver sheen over it.
6. The plant flowers in approximately six weeks from a pinched rooted cutting.
7. When left to reach full bloom, the plant is covered with blossoms which are a pinkish peach in color.
8. Perhaps the most distinguishing feature of Peach Ice over other known double Impatiens cultivars is its clear leaf variegation. The variegation is very stable and does not show signs of yellow as do some sports.

The new cultivar is similar in many respects to the parent cultivar Rosebud Salmon. The primary differences are in the leaf variegation of Peach Ice, and the flower color. The flowers of Peach Ice have a distinct peach tone, as opposed to the light reddish-pink flower color of Rosebud Salmon.

The accompanying colored photographs illustrate the overall appearance of the new cultivar, showing the colors as true as it is reasonably possible to obtain in a colored reproduction of this type. The top photograph is a front view of a fully grown plant of Peach Ice. The bottom photograph is a closeup view showing three flowers and variegated foliage. The illustrated flower color is not precisely shown, appearing somewhat more pink than the true flower color. Reference is made to the flower color values noted below for the correct color.

The following is a detailed description of my new Impatiens cultivar based on plants produced under commercial practice at Loudon, N.H. Color references are made to The Royal Horticultural Society Colour Chart except where general terms of ordinary dictionary significance are used. The color values were determined during cloudy conditions at approximately 12:00 noon under part natural and part inflorescent light in Alexandria, Va.

Parentage: Sport of *Impatiens sultanii,* c.v. Rosebud Salmon.

Propagation:

A. *Type cutting.*—Tip or section (section is always near tip).

B. *Time to initiate roots.*—7 days at 21° C. summer; 7 days at 21° winter.

C. *Rooting habit.*—Good; roots at nodes or internodes; no hormones needed.

Plant description:

A. *Form.*—Mounded form, with some spreading and slight hanging when given space.

B. *Habit of growth.*—Slower, denser growth than its green leaved parent.

C. *Foliage.*—Generally speaking, the foliage color is very unique, being comprised of three colors or shades: green, green with a silver sheen, and a white margin which varies in width, all in varying percentages. 1. Size (mature leaf): Width: 1" to 1¼" Length: 1¼" to 1¾" (excluding petiole). 2. Shape: Ovate, tip acuminate. 3. Texture: Smooth with some wrinkling. 4. Margin: Slightly serrated. 5. Color: Top side 138A-B overlaid with shiny white-grey on surface to provide a grey-green overall effect that is not provided for on The R.H.S. Colour Chart; on immature foliage, edge variegation of 11D, which expands inwardly towards midrib in varying degrees as foliage matures. The underside is 138B-C, with same variegation. The differences in variegation patterns are clearly visible in the photographs, and provide a very attractive appearance. By comparison, the upper surface foliage color of Rosebud Salmon is a solid 137B. 6. Venation: Not distinctive.

Flowering description:

A. *Flowering habits.*—Flowers start as a bud the shape of a round ball and the size of a pea, and open similar to a rose in fullness. The flowers open slightly above or even with the foliage.

B. *Flowering season.*—Year-round in greenhouse environment; best in spring.

C. *Flower buds.*—Basically white with a slight touch of green; peach color comes out as soon as bud cracks open.

D. *Quantity of flowers.*—Varies as to maturity; good flower producer.

E. *Petals.*—Overall inflorescence has an almost rose or camellia type character due to fully double form. 1. Shape: Petals round to slightly oblong with indentation in tip. 2. Color: Upper surface: 38A-B. Lower surface: 38B-C. (The upper surface color of Rosebud Salmon is approximately 51C-D.) 3. Number of petals: Multiple, twenty five or even more. 4. Size of flowers: 1¼" to 2".

F. *Reproductive orangs.*—1. Stamens: Multiple in number; pollen color yellow. 2. Pistils: Stigma color yellow; styles and ovaries not distinctive.

G. *Fragrance.*—None.

Disease resistance: Some resistance to Botrytis. Root fungi are seldom a problem.

I claim:

1. A new and distinct cultivar of *Impatiens sultanii* plant named Peach Ice, as illustrated and described.

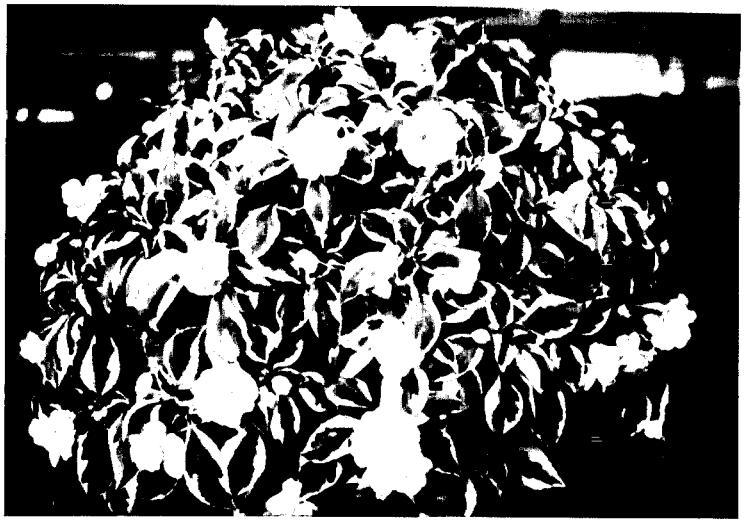
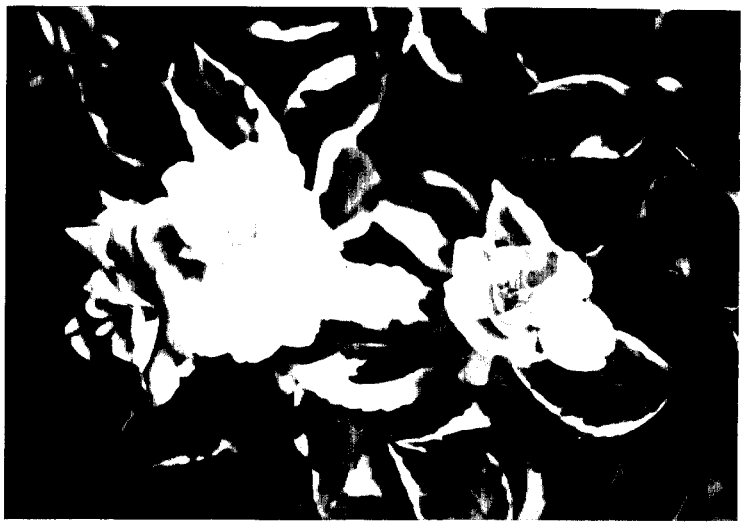

* * * * *